US010351746B2

(12) United States Patent
Fukushima

(10) Patent No.: US 10,351,746 B2
(45) Date of Patent: *Jul. 16, 2019

(54) COMPOSITION FOR HEAT CYCLE SYSTEM, AND HEAT CYCLE SYSTEM

(71) Applicant: AGC Inc., Chiyoda-ku (JP)

(72) Inventor: Masato Fukushima, Chiyoda-ku (JP)

(73) Assignee: AGC Inc., Chiyoda-ku (JP)

(*) Notice: Subject to any disclaimer, the term of this patent is extended or adjusted under 35 U.S.C. 154(b) by 45 days.

This patent is subject to a terminal disclaimer.

(21) Appl. No.: 15/235,994

(22) Filed: Aug. 12, 2016

(65) Prior Publication Data
US 2016/0347981 A1 Dec. 1, 2016

Related U.S. Application Data

(63) Continuation of application No. PCT/JP2015/051410, filed on Jan. 20, 2015.

(30) Foreign Application Priority Data

Feb. 20, 2014 (JP) .................................. 2014-030856

(51) Int. Cl.
C09K 5/04 (2006.01)
C07C 21/18 (2006.01)
(Continued)

(52) U.S. Cl.
CPC .............. C09K 5/045 (2013.01); C07C 21/18 (2013.01); F25B 1/00 (2013.01); F25B 31/002 (2013.01);
(Continued)

(58) Field of Classification Search
CPC .............. C09K 2205/126; C09K 5/045; C09K 2205/22
See application file for complete search history.

(56) References Cited

U.S. PATENT DOCUMENTS

2014/0070132 A1 3/2014 Fukushima
2017/0016660 A1* 1/2017 Nishiyama .............. F25B 9/006
2017/0328586 A1* 11/2017 Maeyama ................ C09K 5/04

FOREIGN PATENT DOCUMENTS

CN 102965082 A 3/2013
CN 103534328 A 1/2014
(Continued)

OTHER PUBLICATIONS

International Search Report dated Apr. 28, 2016 in PCT/JP2015/051410, filed on Jan. 20, 2015.

Primary Examiner — John R Hardee
(74) Attorney, Agent, or Firm — Oblon, McClelland, Maier & Neustadt, L.L.P.

(57) ABSTRACT

To provide a composition for a heat cycle system which comprises a working fluid containing HFO-1123 and having cycle performance sufficient as an alternative to R410A while the influence over global warming is suppressed, and a heat cycle system employing the composition.
A composition for a heat cycle system, which comprises a working fluid for heat cycle containing trifluoroethylene and having a global warming potential (100 years) in Intergovernmental Panel on Climate Change (IPCC), Fourth assessment report, of less than 675, and a heat cycle system employing the composition for a heat cycle system.

12 Claims, 1 Drawing Sheet

(51) Int. Cl.
*F25B 1/00* (2006.01)
*F25B 31/00* (2006.01)

(52) U.S. Cl.
CPC .. *C09K 2205/122* (2013.01); *C09K 2205/126* (2013.01); *C09K 2205/22* (2013.01); *C09K 2205/40* (2013.01); *F25B 2400/12* (2013.01); *Y02B 30/52* (2013.01); *Y02P 20/124* (2015.11)

(56) References Cited

FOREIGN PATENT DOCUMENTS

| EP | 3 101 082 A1 | 12/2016 |
|---|---|---|
| WO | WO 2012/157764 A1 | 11/2012 |
| WO | WO 2015/005290 A1 | 1/2015 |

* cited by examiner

COMPOSITION FOR HEAT CYCLE SYSTEM, AND HEAT CYCLE SYSTEM

TECHNICAL FIELD

The present invention relates to a composition for a heat cycle system and a heat cycle system employing the composition.

BACKGROUND ART

In this specification, abbreviated names of halogenated hydrocarbon compounds are described in brackets after the compound names, and in this specification, the abbreviated names are employed instead of the compound names as the case requires.

Heretofore, as a working fluid for a heat cycle system such as a refrigerant for a refrigerator, a refrigerant for an air-conditioning apparatus, a working fluid for power generation system (such as exhaust heat recovery power generation), a working fluid for a latent heat transport apparatus (such as a heat pipe) or a secondary cooling fluid, a chlorofluorocarbon (CFC) such as chlorotrifluoromethane or dichlorodifluoromethane or a hydrochlorofluorocarbon (HCFC) such as chlorodifluoromethane has been used. However, influences of CFCs and HCFCs over the ozone layer in the stratosphere have been pointed out, and their use is regulated at present.

Under the above conditions, as a working fluid for a heat cycle system, a hydrofluorocarbon (HFC) which has less influence over the ozone layer, such as difluoromethane (HFC-32), tetrafluoroethane or pentafluoroethane (HFC-125) has been used, instead of CFCs and HCFCs. For example, R410A (a pseudoazeotropic mixture refrigerant of HFC-32 and HFC-125 in a mass ratio of 1:1) is a refrigerant which has been widely used. However, it is pointed out that HFCs may cause global warming.

R410A has been widely used for a common air-conditioning apparatus such as a so-called package air-conditioner or room air-conditioner, due to its high refrigerating capacity. However, it has a global warming potential (GWP) of so high as 2,088, and accordingly development of a working fluid with low GWP has been desired. Further, development of a working fluid has been desired on the condition that R410A is simply replaced and existing apparatus will be used as they are.

In recent years, a hydrofluoroolefin (HFO) i.e. a HFC having a carbon-carbon double bond is expected, which is a working fluid having less influence over the ozone layer and having less influence over global warming, since the carbon-carbon double bond is likely to be decomposed by OH radicals in the air. In this specification, a saturated HFC will be referred to as a HFC and distinguished from a HFO unless otherwise specified. Further, a HFC may be referred to as a saturated hydrofluorocarbon in some cases.

As a working fluid employing a HFO, for example, Patent Document 1 discloses a technique relating to a working fluid using 1,1,2-trifluoroethylene (HFO-1123) which has the above properties and with which excellent cycle performance will be obtained. Patent Document 1 also discloses an attempt to obtain a working fluid comprising HFO-1123 and various HFCs or HFOs in combination for the purpose of increasing the flame retardancy, cycle performance, etc. of the working fluid.

However, Patent document 1 failed to disclose or suggest to combine HFO-1123 with a HFC or another HFO to obtain a working fluid, with a view to obtaining a working fluid which is practically useful as an alternative to R410A comprehensively considering the balance of the performance, the efficiency and the temperature glide.

PRIOR ART DOCUMENT

Patent Document

Patent Document 1: WO2012/157764

DISCLOSURE OF INVENTION

Technical Problem

It is an object of the present invention to provide a composition for a heat cycle system comprising a working fluid which contains HFO-1123 and which has cycle performance sufficient as an alternative to R410A while the influence over global warming is sufficiently suppressed, and a heat cycle system employing the composition.

Solution to Problem

The present invention provides a composition for a heat cycle system and a heat cycle system of the following [1] to [15].

[1] A composition for a heat cycle system, which comprises a working fluid for heat cycle containing HFO-1123 and having a global warming potential (100 years) in Intergovernmental Panel on Climate Change (IPCC), Fourth assessment report, of less than 675.

[2] The composition for a heat cycle system according to [1], wherein of the working fluid for heat cycle, the relative coefficient of performance ($RCOP_{R410A}$) calculated in accordance with the following formula (1) is from 0.85 to 1.20:

$$\text{Relative performance of coefficient } (RCOP_{R410A}) = \frac{\text{Coefficient of performance of sample } (COP_{sample})}{\text{Coefficient of performance of } R410A \ (COP_{R410A})} \quad (1)$$

wherein R410A is a mixture of HFC-32 and HFC-125 in a mass ratio of 1:1, and the sample is the working fluid to be subjected to relative evaluation; and the coefficient of performance of each of the sample and R410A is a value obtained by dividing the obtained output (kW) by the required power consumption (kW) when each of the sample and R410A is applied to a standard refrigerating cycle under conditions such that the evaporation temperature is −15° C. (in the case of a non-azeotropic mixture, the average temperature of the evaporation initiation temperature and the evaporation completion temperature), the condensing temperature is 30° C. (in the case of a non-azeotropic mixture, the average temperature of the condensation initiation temperature and the condensation completion temperature), the supercooling degree (SC) is 5° C., and the degree of superheat (SH) is 0° C.

[3] The composition for a heat cycle system according to [1] or [2], wherein of the working fluid for heat cycle, the relative refrigerating capacity ($RQ_{R410A}$) calculated in accordance with the following formula (2) is from 0.70 to 1.50:

$$\text{Relative refrigerating capacity } (RQ_{R410A}) = \frac{\text{Refrigerating capacity of sample } (Q_{sample})}{\text{Refrigerating capacity of R410A } (Q_{R410A})} \quad (2)$$

wherein R410A is a mixture of HFC-32 and HFC-125 in a mass ratio of 1:1, and the sample is the working fluid to be subjected to relative evaluation; and the refrigerating capacity of each of the sample and R410A is an output (kW) when each of the sample and R410A is applied to a standard refrigerating cycle under conditions such that the evaporation temperature is −15° C. (in the case of a non-azeotropic mixture, the average temperature of the evaporation initiation temperature and the evaporation completion temperature), the condensing temperature is 30° C. (in the case of a non-azeotropic mixture, the average temperature of the condensation initiation temperature and the condensation completion temperature), the supercooling degree (SC) is 5° C., and the degree of superheat (SH) is 0° C.

[4] The composition for a heat cycle system according to any one of [1] to [3], wherein of the working fluid for heat cycle, the temperature glide is at most 8° C., which is represented by a difference between the evaporation initiation temperature and the evaporation completion temperature in an evaporator when applied to a standard refrigerating cycle under conditions such that the evaporation temperature is −15° C. (in the case of a non-azeotropic mixture, the average temperature of the evaporation initiation temperature and the evaporation completion temperature), the condensing temperature is 30° C. (in the case of a non-azeotropic mixture, the average temperature of the condensation initiation temperature and the condensation completion temperature), the supercooling degree (SC) is 5° C., and the degree of superheat (SH) is 0° C.

[5] The composition for a heat cycle system according to any one of [1] to [4], wherein the value (TΔ) is at most 30° C., which is obtained by subtracting the compressor discharge gas temperature ($T_{R410A}$) when a mixture of HFC-32 and HFC-125 in a mass ratio of 1:1 is applied to the following standard refrigerating cycle, from the compressor discharge gas temperature (Tx) when the working fluid for heat cycle is applied to the following standard refrigerating cycle, the standard refrigerating cycle being conducted under conditions such that the evaporation temperature is −15° C. (in the case of a non-azeotropic mixture, the average temperature of the evaporation initiation temperature and the evaporation completion temperature), the condensing temperature is 30° C. (in the case of a non-azeotropic mixture, the average temperature of the condensation initiation temperature and the condensation completion temperature), the supercooling degree (SC) is 5° C., and the degree of superheat (SH) is 0° C.

[6] The composition for a heat cycle system according to any one of [1] to [5], wherein the working fluid for heat cycle has a heat of combustion of less than 19 MJ/kg.

[7] The composition for a heat cycle system according to any one of [1] to [6], wherein the working fluid for heat cycle contains HFO-1123, a saturated hydrofluorocarbon and HFO-1234ze.

[8] The composition for a heat cycle system according to [7], wherein the saturated hydrofluorocarbon is HFC-32, HFC-152a, HFC-134a or HFC-125.

[9] The composition for a heat cycle system according to [7], wherein the saturated hydrofluorocarbon is HFC-32.

[10] The composition for a heat cycle system according to [9], wherein the proportion of HFO-1123 is from 10 to 80 mass %, the proportion of HFC-32 is from 10 to 80 mass %, and the proportion of HFO-1234ze is from 5 to 45 mass %, based on the working fluid for heat cycle.

[11] The composition for a heat cycle system according to any one of [1] to [10], wherein the proportion of HFO-1123 is at least 20 mass % based on the working fluid for heat cycle.

[12] The composition for a heat cycle system according to any one of [1] to [11], wherein the proportion of HFO-1123 is from 20 to 80 mass % based on the working fluid for heat cycle.

[13] The composition for a heat cycle system according to any one of [1] to [12], wherein the proportion of HFO-1123 is from 40 to 60 mass % based on the working fluid for heat cycle.

[14] A heat cycle system, which employs the composition for a heat cycle system as defined in any one of [1] to [13].

[15] The heat cycle system according to [14], which is a refrigerating apparatus, an air-conditioning apparatus, a power generation system, a heat transport apparatus or a secondary cooling machine.

Advantageous Effects of Invention

According to the present invention, it is possible to provide a composition for a heat cycle system, which comprises a working fluid for heat cycle containing HFO-1123 and having cycle performance sufficient as an alternative to R410A while the influence over global warming is suppressed.

The heat cycle system of the present invention is a heat cycle system which employs a composition for a heat cycle system which can replace R410A and which has less influence over global warming potential.

DESCRIPTION OF EMBODIMENTS

Figure 1:
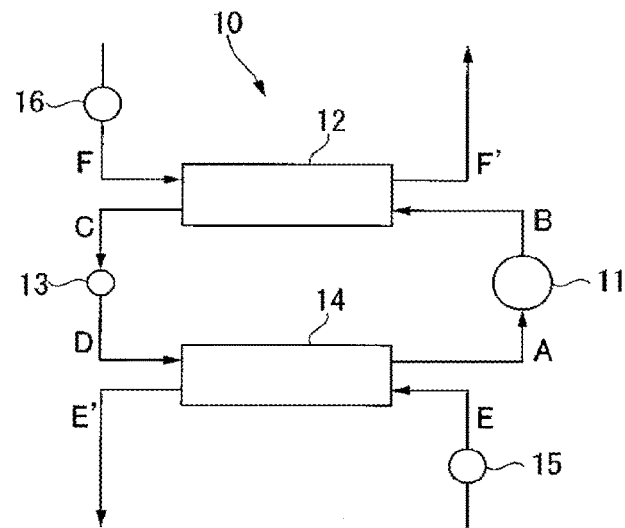
FIG. 1 is a schematic construction view illustrating an example of a standard refrigerating cycle system to evaluate the heat cycle system of the present invention.

Now, the present invention will be described in detail.

[Composition for Heat Cycle System]

The composition for a heat cycle system of the present invention comprises a working fluid for heat cycle (hereinafter sometimes referred to simply as "working fluid") containing HFO-1123 and having a global warming potential (100 years) in Intergovernmental Panel on Climate Change (IPCC), Fourth assessment report, of less than 675.

In the composition for a heat cycle system of the present invention, as a working fluid which can be used as an alternative to R410A while the influence over global warming is suppressed, a working fluid containing HFO-1123 is employed.

(A) Global Warming Potential (GWP)

In the present invention, as an index to the influence of the working fluid over global warming, GWP is employed. In this specification, GWP is a value (100 years) in Intergovernmental Panel on Climate Change (IPCC), Fourth assessment report (2007), unless otherwise specified. Further, GWP of a mixture is represented by a weighted average by the composition mass.

The global warming potential (100 years) of HFO-1123 which the working fluid of the present invention contains is 0.3 as a value measured in accordance with IPCC Fourth assessment report. This value is remarkably small as compared with GWPs of other HFOs, for example, GWP of HFO-1234ze(E) of 6, and GWP of HFO-1234yf of 4.

Further, R410A (a composition of HFC-125 and HFC-32 in a mass ratio of 1:1) which is excellent in the cycle performance, to be replaced by the working fluid of the present invention, has an extremely high GWP of 2,088, and the two HFCs contained in R410A and other typical HFCs, for example, HFC-134a, have high GWP as shown in the following Table 1.

TABLE 1

| Compound | GWP |
|---|---|
| R410A | 2088 |
| HFO-1123 | 0.3 |
| HFO-1234yf | 4 |
| HFO-1234ze(E) | 6 |
| HFC-32 | 675 |
| HFC-134a | 1430 |
| HFC-125 | 3500 |

Here, as a property required when a certain working fluid is applied to heat cycle, the cycle performance may be evaluated by the coefficient of performance (also referred to as "COP" in this specification) and the capacity (also referred to as "Q" in this specification). In a case where the heat cycle system is a refrigerating cycle system, the capacity is refrigerating capacity. As items to be evaluated when the working fluid is applied to a refrigerating cycle system, in addition to the above cycle performance, the temperature glide and the compressor discharge gas temperature may further be mentioned. In the present invention, the performance of the working fluid is evaluated with reference to the above four items as indices. Specifically, a standard refrigerating cycle system under the following temperature conditions is conducted, the respective items are measured by the after-mentioned methods for example, and except for the temperature glide, the measured values are calculated into relative values based on the values of R410A to be replaced. Now, the following items to be evaluated will be described in detail.

(Temperature Conditions for Standard Refrigerating Cycle)

Evaporation temperature: −15° C. (in the case of a non-azeotropic mixture, the average temperature of the evaporation initiation temperature and the evaporation completion temperature)

Condenssing temperature: 30° C. (in the case of a non-azeotropic mixture, the average temperature of the condensation initiation temperature and the condensation completion temperature)

Supercooling degree (SC): 5° C.

Degree of superheat (SH): 0° C.

(B) Relative Refrigerating Capacity (Hereinafter Sometimes Referred to as "$RQ_{R410A}$")

The refrigerating capacity is an output in the refrigerating cycle system. The relative refrigerating capacity relative to R410A may be obtained in accordance with the following formula (2). In the formula (2), the sample is the working fluid to be subjected to relative evaluation.

$$\text{Relative refrigerating capacity } (RQ_{R410A}) = \frac{\text{Refrigerating capacity of sample } (Q_{sample})}{\text{Refrigerating capacity of } R410A \ (Q_{R410A})} \quad (2)$$

(C) Relative Coefficient of Performance (Hereinafter Sometimes Referred to as "$RCOP_{R410A}$")

The coefficient of performance is a value obtained by dividing an output (kW) by the power (kW) consumed to obtain the output (kW) and corresponds to the energy consumption efficiency. A higher output will be obtained with a low input when the coefficient of performance is higher. The relative coefficient of performance relative to R410A may be obtained in accordance with the following formula (1). In the formula (1), the sample is a working fluid to be subjected to relative evaluation.

$$\text{Relative performance of coefficient } (RCOP_{R410A}) = \frac{\text{Coefficient of performance of sample } (COP_{sample})}{\text{Coefficient of performance of } R410A \ (COP_{R410A})} \quad (1)$$

(D) Temperature Glide

The temperature glide is an index to a difference in the composition between in a liquid phase and in a gaseous phase of a mixture as the working fluid. The temperature glide is defined as properties such that the initiation temperature and the completion temperature of evaporation in an evaporator or of condensation in a condenser, for example, as the heat exchanger, differ from each other. The temperature glide of an azeotropic mixture fluid is 0, and the temperature glide of a pseudoazeotropic mixture such as R410A is extremely close to 0.

If the temperature glide is large, for example, the inlet temperature of an evaporator tends to be low, and frosting is likely to occur. Further, in a heat cycle system, the heat exchange efficiency is to be improved by making the working fluid and the heat source fluid such as water or the air flowing in heat exchangers flow in counter-current flow. Since the temperature difference of the heat source fluid is small in a stable operation state, it is difficult to obtain a heat cycle system with a good energy efficiency with a non-azeotropic mixture fluid with a large temperature glide. Accordingly, in a case where a mixture is used as the working fluid, a working fluid with an appropriate temperature glide is desired.

Further, when a non-azeotropic mixture fluid is put into a refrigerator or an air-conditioning apparatus from a pressure container, it undergoes a composition change. Further, if a refrigerant leaks out from a refrigerator or an air-conditioning apparatus, the refrigerant composition in the refrigerator or the air-conditioning apparatus is very likely to change, and a recovery to an initial refrigerant composition is hardly possible. Whereas, the above problems can be avoided with an azeotropic or pseudoazeotropic mixture fluid.

(E) Compressor Discharge Gas Temperature Difference TΔ

A value (TΔ) obtained by subtracting the compressor discharge gas temperature ($T_{R410A}$) of R410A from the compressor discharge gas temperature (Tx) of a sample i.e. the working fluid to be subjected to relative evaluation, is evaluated. The compressor discharge gas temperature (hereinafter sometimes referred to as "discharge temperature") in refrigerating cycle is the maximum temperature in the refrigerating cycle. The discharge temperature, which has influence over the material constituting a compressor, a refrigerant oil which the composition for a heat cycle system usually contains in addition to the working fluid, and the heat resistance of a polymer material, is preferably lower. In order that the working fluid is useful as an alternative to R410A, the discharge temperature should be a temperature which equipment constituting the heat cycle system operated with R410A can withstand, whether it may be lower or higher than the discharge temperature of R410A.

The results of evaluation of the four items (B) to (E) and the above (A) GWP with respect to HFO-1123 are shown in Table 2 together with the results with respect to R410A. Further, the results with respect to HFC-32 having the lowest GWP among HFCs which can be safely used by themselves, are shown in Table 2.

HFO-1123 has a very low GWP as mentioned above. However, when it is used as an alternative to R410A for a heat cycle system, further improvement with respect to $RCOP_{R410A}$ may sometimes be required when HFO-1123 is used by itself as shown in the following Table 2.

To obtain a working fluid, considering the improvement in the cycle performance and influence over global warming, it is common to use a mixed fluid of two or more compounds, such as R410A. With respect to HFO-1123 also, it is formed into various compositions depending upon the application considering the cycle performance, the temperature glide, the influence over global warming, and the like in a balanced manner.

HFO-1123, which has a very low GWP as mentioned above, has an advantage over other HFOs in that when it is combined with a HFC having high cycle performance and having a high GWP to obtain a mixed composition for the purpose of improving the cycle performance, etc., the cycle performance can be improved while GWP is kept low. Further, the HFO-1123 working fluid to be used for the composition for a heat cycle system of the present invention is a working fluid having low GWP of less than 675, which cannot be achieved by a HFC.

more preferably at most 8° C., further preferably at most 5° C., particularly preferably at most 3° C., most preferably at most 1° C.

(E) Discharge temperature difference TΔ is preferably at most 30° C., more preferably at most 20° C., particularly preferably at most 10° C.

The relation of preferred ranges of the items (A) to (E) is shown in Table 3. In Table 3, with respect to each item, the preferred condition range is limited in the order of (1)→(2)→(3)→(4). (4) represents the most preferred range. Table 3 further shows a condition of (F) heat of combustion of less than 19 MJ/kg. The heat of combustion represents the amount of heat generated with the combustion reaction, and if a sample has a heat of combustion of at least 19 MJ/kg, such a sample is classified into a group "higher flammability" in ASHRAE standard 34, and thus the heat of combustion is preferably less than 19 MJ/kg.

TABLE 3

| Physical properties/condition | (1) | (2) | (3) | (4) |
|---|---|---|---|---|
| (A) GWP | <675 | ≤500 | ≤300 | ≤150 |
| (B) Relative refrigerating capacity ($RQ_{R410A}$) | 0.70 to 1.50 | 0.90 to 1.50 | 1.00 to 1.50 | |
| (C) Relative coefficient of performance ($RCOP_{R410A}$) | 0.85 to 1.20 | 0.90 to 1.20 | 0.95 to 1.20 | |
| (D) Temperature glide [° C.] | ≤8 | ≤5 | ≤3 | ≤1 |
| (E) Compressor discharge gas temperature difference TΔ [° C.] | ≤30 | ≤20 | ≤10 | |
| (F) Heat of combustion [MJ/kg] | <19 | | | |

The working fluid containing HFO-1123 used in the present invention is require to satisfy the condition (A)-(1) in Table 3. Except for this condition, the combination of the levels of the respective items is not particularly limited. Most preferred is a working fluid which satisfies all the conditions of (A)-(4), (B)-(3), (C)-(3), (D)-(4), (E)-(3) and (F)-(1).

As the refrigerating cycle system employed for the above evaluation, for example, a refrigerating cycle system of

TABLE 2

| Compound | Global warming potential (A) GWP | Cycle performance | | Composition change | Maximum temperature in system |
| | | (B) Relative refrigerating capacity $RQ_{R410A}$ | (C) Relative coefficient of performance $RCOP_{R410A}$ | (D) Temperature glide [° C.] | (E) Discharge temperature difference TΔ [° C.] |
|---|---|---|---|---|---|
| R410A | 2088 | 1.00 | 1.00 | 0.0 | 0.0 |
| HFO-1123 | 0.3 | 1.17 | 0.95 | 0.0 | 3.4 |
| HFC-32 | 675 | 1.10 | 1.01 | 0.0 | 22.5 |

The working fluid containing HFO-1123 used in the present invention has GWP<675. GWP is preferably at most 500, more preferably at most 300, particularly preferably at most 150.

Further, the working fluid containing HFO-1123 used in the present invention preferably has (B) relative refrigerating capacity $RQ_{R410A}$ of preferably from 0.70 to 1.50, more preferably from 0.90 to 1.50, particularly preferably from 1.00 to 1.50.

(C) Relative coefficient of performance $RCOP_{R410A}$ is preferably from 0.85 to 1.20, more preferably from 0.90 to 1.20, particularly preferably from 0.95 to 1.20. (D) Temperature glide is at most 11° C., preferably at most 9° C., which the schematic construction view is shown in FIG. 1, may be used. Now, the method for evaluating the cycle performance, the temperature glide and the compressor discharge gas temperature (Tx) employing the refrigerating cycle system shown in FIG. 1 will be described.

A refrigerating cycle system 10 shown in FIG. 1 is a system generally comprising a compressor 11 to compress a working fluid vapor A to form a high temperature/high pressure working fluid vapor B, a condenser 12 to cool and liquefy the working fluid vapor B discharged from the compressor 11 to form a low temperature/high pressure working fluid C, an expansion valve 13 to let the working fluid C discharged from the condenser 12 expand to form a low temperature/low pressure working fluid D, an evaporator 14 to heat the working fluid D discharged from the expansion valve 13 to form a high temperature/low pressure working fluid vapor A, a pump 15 to supply a load fluid E to the evaporator 14, and a pump 16 to supply a fluid F to the condenser 12.

In the refrigerating cycle system 10, a cycle of the following (i) to (iv) is repeated.

(i) A working fluid vapor A discharged from an evaporator 14 is compressed by a compressor 11 to form a high temperature/high pressure working fluid vapor B (hereinafter referred to as "AB process").

(ii) The working fluid vapor B discharged from the compressor 11 is cooled and liquefied by a fluid F in a condenser 12 to form a low temperature/high pressure working fluid C. At that time, the fluid F is heated to form a fluid F', which is discharged from the condenser 12 (hereinafter referred to as "BC process").

(iii) The working fluid C discharged from the condenser 12 is expanded in an expansion valve 13 to form a low temperature/low pressure working fluid D (hereinafter referred to as "CD process").

(iv) The working fluid D discharged from the expansion valve 13 is heated by a load fluid E in the evaporator 14 to form a high temperature/low pressure working fluid vapor A. At that time, the load fluid E is cooled and becomes a load fluid E', which is discharged from the evaporator 14 (hereinafter referred to as "DA process").

The refrigerating cycle system 10 is a cycle system comprising an adiabatic isentropic change, an isenthalpic change and an isobaric change. The state change of the working fluid, as represented on a pressure-enthalpy diagram (curve) as shown in FIG. 2, may be represented as a trapezoid having points A, B, C and D as vertexes.

Figure 2:
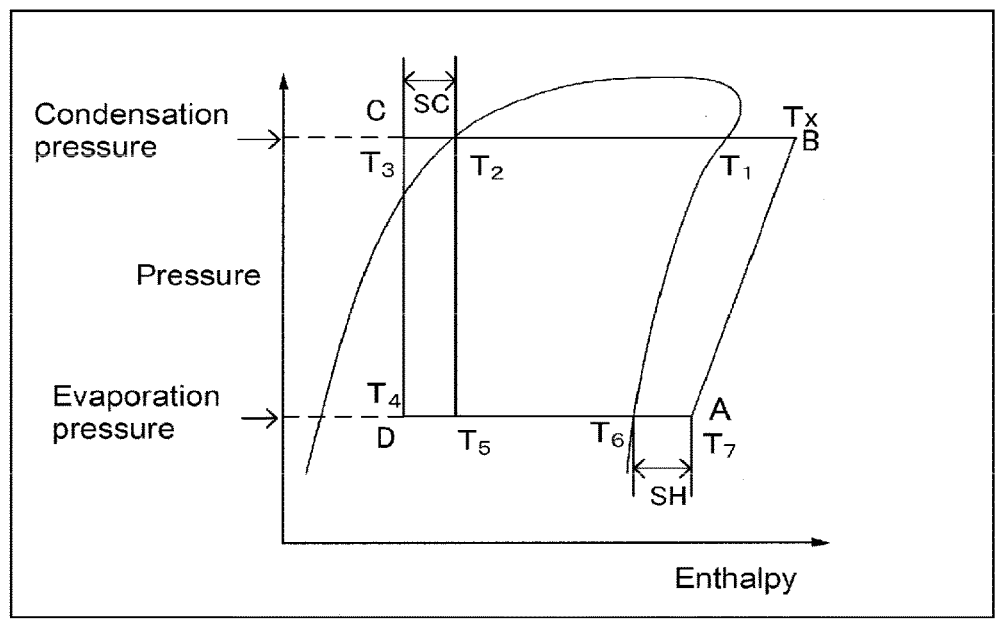
FIG. 2 is a cycle diagram illustrating the state change of the working fluid in a refrigerating cycle system in FIG. 1 on a pressure-enthalpy diagram.

The AB process is a process wherein adiabatic compression is carried out by the compressor 11 to change the high temperature/low pressure working fluid vapor A to a high temperature/high pressure working fluid vapor B, and is represented by the line AB in FIG. 2. As described hereinafter, the working fluid vapor A is introduced to the compressor 11 in a superheated state, and the obtainable working fluid vapor B is also a superheated vapor. The compressor discharge gas temperature (discharge temperature) is the temperature (Tx) in the state B in FIG. 2 and is the maximum temperature in the refrigerating cycle.

The BC process is a process wherein isobaric cooling is carried out in the condenser 12 to change the high temperature/high pressure working fluid vapor B to a low temperature/high pressure working fluid C and is represented by the BC line in FIG. 2. The pressure in this process is the condensation pressure. Of the two intersection points of the pressure-enthalpy diagram and the BC line, the intersection point $T_1$ on the high enthalpy side is the condensing temperature, and the intersection point $T_2$ on the low enthalpy side is the condensation boiling point temperature. In a case where the working fluid is a non-azeotropic mixture fluid, the temperature glide is represented by a difference between $T_1$ and $T_2$.

The CD process is a process wherein isenthalpic expansion is carried out by the expansion valve 13 to change the low temperature/high pressure working fluid C to a low temperature/low pressure working fluid D and is presented by the CD line in FIG. 2. $T_2$-$T_3$ corresponds to the supercooling degree (SC) of the working fluid in the cycle of (i) to (iv), where $T_3$ is the temperature of the low temperature/high pressure working fluid C.

The DA process is a process wherein isobaric heating is carried out in the evaporator 14 to have the low temperature/low pressure working fluid D returned to a high temperature/low pressure working fluid vapor A, and is represented by the DA line in FIG. 2. The pressure in this process is the evaporation pressure. Of the two intersection points of the pressure-enthalpy diagram and the DA line, the intersection point $T_6$ on the high enthalpy side is the evaporation temperature. $T_7$-$T_6$ corresponds to the degree of superheat (SH) of the working fluid in the cycle of (i) to (iv), where $T_7$ is the temperature of the working fluid vapor A. $T_4$ indicates the temperature of the working fluid D.

Q and COP of the working fluid are obtained respectively in accordance with the following formulae (11) and (12) from enthalpies $h_A$, $h_B$, $h_C$ and $h_D$ in the respective states A (after evaporation, high temperature and low pressure), B (after compression, high temperature and high pressure), C (after condensation, low temperature and high pressure) and D (after expansion, low temperature and low pressure) of the working fluid.

It is assumed that there is no loss in the equipment efficiency and no pressure loss in the pipelines and heat exchangers.

The thermodynamic properties required for calculation of the cycle performance of the working fluid are calculated based on the generalized equation of state (Soave-Redlich-Kwong equation) based on the law of corresponding state and various thermodynamic equations. If a characteristic value is not available, it is calculated employing an estimation technique based on a group contribution method.

$$Q = h_A - h_D \tag{11}$$

$$\text{COP} = Q/\text{compression work} = (h_A - h_D)/(h_B - h_A) \tag{12}$$

Q represented by the above ($h_A$-$h_D$) corresponds to the output (kW) of the refrigerating cycle, and the compression work represented by ($h_B$-$h_A$), for example, an electric energy required to operate a compressor, corresponds to the power (kW) consumed. Further, Q means a capacity to freeze a load fluid, and a higher Q means that more works can be done in the same system. In other words, it means that with a working fluid having a higher Q, the desired performance can be obtained with a smaller amount, whereby the system can be downsized.

As the heat cycle system to which the composition for a heat cycle system of the present invention is applied, a heat cycle system by heat exchangers such as a condenser and an evaporator may be used without any particularly restriction. The heat cycle system, for example, refrigerating cycle, has a mechanism in which a gaseous working fluid is compressed by a compressor and cooled by a condenser to form a high pressure liquid, the pressure of the liquid is lowered by an expansion valve, and the liquid is vaporized at low temperature by an evaporator so that heat is removed by the heat of vaporization.

<Composition of Working Fluid>

The composition for a heat cycle system of the present invention comprises a working fluid containing HFO-1123, and the working fluid has GWP of less than 675.

The working fluid according to the present invention may contain, in addition to HFO-1123, as the case requires, the following optional component. The content of HFO-1123 per 100 mass % of the working fluid is preferably at least 20 mass %, more preferably from 20 to 80 mass %, further preferably from 40 to 60 mass %.

The optional component may, for example, be a HFC, a HFO (a HFC having a carbon-carbon double bond) other than HFO-1123, or another component which is vaporized and liquefied together with HFO-1123. The optional component is preferably a HFC or a HFO (a HFC having a carbon-carbon double bond) other than HFO-1123.

The optional component is preferably a compound, when used in combination with HFO-1123 for heat cycle, which can further increase the relative coefficient of performance and the relative refrigerating capacity and which can keep GWP, the temperature glide and the discharge temperature difference TΔ within acceptable ranges. When the working fluid contains such a compound in combination with HFO-1123, more favorable cycle performance will be obtained while GWP is kept low, and there is little influence by the temperature glide or the discharge temperature difference.
(HFC)

The HFC as the optional component is preferably selected from the above viewpoint. The HFC to be combined with HFO-1123 is preferably selected properly with a view to improving the cycle performance as the working fluid, keeping the temperature glide to be within an appropriate range and in addition, particularly, keeping GWP to be within an acceptable range.

The HFC which has less influence over the ozone layer and which has less influence over global warming is specifically preferably a $C_{1-5}$ HFC. The HFC may be linear, branched or cyclic.

The HFC may, for example, be difluoromethane (HFC-32), difluoroethane, trifluoroethane, tetrafluoroethane, pentafluoroethane (HFC-125), pentafluoropropane, hexafluoropropane, heptafluoropropane, pentafluorobutane or heptafluorocyclopentane.

Among them, in view of less influence over the ozone layer and excellent refrigerating cycle property, the HFC is preferably HFC-32, 1,1-difluoroethane (HFC-152a), 1,1,1-trifluoroethane (HFC-143a), 1,1,2,2-tetrafluoroethane (HFC-134), 1,1,1,2-tetrafluoroethane (HFC-134a) or HFC-125, more preferably HFC-32, HFC-152a, HFC-134a or HFC-125.

The HFC may be used alone or in combination of two or more.

The content of the HFC in the working fluid (100 mass %) may be optionally selected depending upon the required properties of the working fluid. For example, in the case of a working fluid consisting of HFO-1123 and HFC-32, the relative coefficient of performance will improve within a range of the HFC-32 content of from 1 to 99 mass %. In the case of a working fluid consisting of HFO-1123 and HFC-134a, the relative coefficient of performance will improve while GWP is kept to be within the above range, at a HFC-134a content of from 1 to 47 mass %.

Further, with a view to keeping GWP of the obtained working fluid low, the HFC as the optional component is most preferably HFC-32.

Further, HFO-1123 and HFC-32 may form a pseudoazeotropic mixture close to an azeotropic mixture within a composition range of from 99:1 to 1:99 by the mass ratio, and the temperature glide of the mixture of them is close to 0 substantially regardless of the composition range. In this view also, the HFC-32 is advantageous as the HFC to be combined with HFO-1123.

In a case where the working fluid used in the present invention contains HFC-32 together with HFO-1123, the content of HFC-32 per 100 mass % of the working fluid is specifically preferably at least 20 mass %, more preferably from 20 to 80 mass %, further preferably from 40 to 60 mass %.
(HFO Other than HFO-1123)

The HFO other than HFO-1123 as an optional component is also preferably selected from the same viewpoint as the above HFC. Here, GWP of the HFO even other than HFO-1123 is an order of magnitude lower than the HFC. Accordingly, as the HFO other than HFO-1123 used in combination with HFO-1123 is preferably selected properly particularly with a view to improving the cycle performance as the working fluid and keeping the temperature glide and the discharge temperature difference TΔ within appropriate ranges, rather than considering GWP.

The HFO other than HFO-1123 may, for example, be 2,3,3,3-tetrafluoropropene (HFO-1234yf), 1,2-difluoroethylene (HFO-1132), 2-fluoropropene (HFO-1261yf), 1,1,2-trifluoropropene (HFO-1243yc), trans-1,2,3,3,3-pentafluoropropene (HFO-1225ye(E)), cis-1,2,3,3,3-pentafluoropropene (HFO-1225ye(Z)), trans-1,3,3,3-tetrafluoropropene (HFO-1234ze(E)), cis-1,3,3,3-tetrafluoropropene (HFO-1234ze(Z)) or 3,3,3-trifluoropropene (HFO-1243zf).

In the present invention, HFO-1234ze(E) and HFO-1234ze(Z) will sometimes generally be referred to as 1,3,3,3-tetrafluoropropene (HFO-1234ze).

Particularly, the HFO other than HFO-1123 is, in view of a high critical temperature and excellent safety and coefficient of performance, preferably HFO-1234yf, HFO-1234ze(E) or HFO-1234ze(Z), more preferably HFO-1234yf or HFO-1234ze(E). The HFO is particularly preferably HFO-1234ze(E). The HFO other than HFO-1123 may be used alone or in combination of two or more.

The content of the HFO other than HFO-1123 in the working fluid (100 mass %) may be optionally selected depending upon the required properties of the working fluid. For example, in the case of a working fluid consisting of HFO-1123 and HFO-1234yf or HFO-1234ze, the coefficient of performance will improve within a range of the HFO-1234yf or HFO-1234ze content of from 1 to 99 mass %.

In the case of a working fluid comprising HFO-1123 and HFO-1234yf, for example, a working fluid having a proportion of the total amount of HFO-1123 and HFO-1234yf (or HFO-1234ze) based on the entire amount of the working fluid of from 70 to 100 mass % and a proportion of HFO-1234yf (or HFO-1234ze) based on the total amount of HFO-1123 and HFO-1234yf (or HFO-1234ze) of from 5 to 65 mass % is preferred in view of the balance of the cycle performance, the temperature glide, the discharge temperature difference and GWP.

The working fluid used in the present invention may be a combination of HFO-1123, a HFC and a HFO other than HFO-1123. In such a case, the working fluid is preferably a working fluid containing HFO-1123, HFC-32 and HFO-1234yf (or HFO-1234ze).

In a case where the HFO other than HFO-1123 is HFO-1234yf, the proportions of the respective compounds based on the entire amount of the working fluid containing HFO-1123, HFC-32 and HFO-1234yf are more preferably within the following ranges.

20 mass %≤HFO-1123≤80 mass %

10 mass %≤HFC-32≤75 mass %

5 mass %≤HFO-1234yf≤50 mass %

The working fluid containing HFO-1123, HFC-32 and HFO-1234yf is more preferably a working fluid consisting of HFO-1123, HFC-32 and HFO-1234yf.

Further, in a case where the HFO other than HFO-1123 is HFO-1234ze, the proportions of the respective compounds based on the entire amount of the working fluid containing HFO-1123, HFC-32 and HFO-1234ze are more preferably within the following ranges.

10 mass %≤HFO-1123≤80 mass %

10 mass %≤HFC-32≤80 mass %

5 mass %≤HFO-1234ze≤45 mass %

The working fluid containing HFO-1123, HFC-32 and HFO-1234ze is more preferably a working fluid consisting of HFO-1123, HFC-32 and HFO-1234ze. Further, HFO-1234ze is preferably HFO-1234ze(E).

<Other Optional Component>

The working fluid to be used for the composition for a heat cycle system of the present invention may contain, other than the above optional component, carbon dioxide, a hydrocarbon, a chlorofluoroolefin (CFO), a hydrochlorofluoroolefin (HCFO) or the like. Such other optional component is preferably a component which has less influence over the ozone layer and which has less influence over global warming.

The hydrocarbon may, for example, be propane, propylene, cyclopropane, butane, isobutane, pentane or isopentane.

The hydrocarbon may be used alone or in combination of two or more.

In a case where the working fluid contains a hydrocarbon, its content is less than 10 mass %, preferably from 1 to 5 mass %, more preferably from 3 to 5 mass % per 100 mass % of the working fluid. When the content of the hydrocarbon is at least the lower limit, the solubility of a mineral refrigerant oil in the working fluid will be favorable.

The CFO may, for example, be chlorofluoropropene or chlorofluoroethylene. With a view to suppressing flammability of the working fluid without significantly decreasing the cycle performance of the working fluid, the CFO is preferably 1,1-dichloro-2,3,3,3-tetrafluoropropene (CFO-1214ya), 1,3-dichloro-1,2,3,3-tetrafluoropropene (CFO-1214yb) or 1,2-dichloro-1,2-difluoroethylene (CFO-1112).

The CFO may be used alone or in combination of two or more.

In a case where the working fluid contains the CFO, its content is less than 10 mass %, preferably from 1 to 8 mass %, more preferably from 2 to 5 mass % per 100 mass % of the working fluid. When the content of the CFO is at least the lower limit, the flammability of the working fluid tends to be suppressed. When the content of the CFO is at most the upper limit, favorable cycle performance is likely to be obtained.

The HCFO may, for example, be hydrochlorofluoropropene or hydrochlorofluoroethylene. With a view to suppressing the flammability of the working fluid without significantly decreasing the cycle performance of the working fluid, the HCFO is preferably 1-chloro-2,3,3,3-tetrafluoropropene (HCFO-1224yd) or 1-chloro-1,2-difluoroethylene (HCFO-1122).

The HCFO may be used alone or in combination of two or more.

In a case where the working fluid contains the HCFO, the content of the HCFO per 100 mass % of the working fluid is less than 10 mass %, preferably from 1 to 8 mass %, more preferably from 2 to 5 mass %. When the content of the HCFO is at least the lower limit, the flammability of the working fluid tends to be suppressed. When the content of the HCFO is at most the upper limit, favorable cycle performance is likely to be obtained.

In a case where the working fluid used for the composition for a heat cycle system of the present invention contains the above other optional component, the total content of such other optional component in the working fluid is less than 10 mass %, preferably at most 8 mass %, more preferably at most 5 mass % per 100 mass % of the working fluid.

The composition for a heat cycle system of the present invention contains, in addition to the above working fluid, a refrigerant oil, in the same manner as a conventional composition for a heat cycle system. The composition for a heat cycle system comprising the working fluid and a refrigerant oil may further contain known additives such as a stabilizer and a leak detecting substance.

<Refrigerant Oil>

As a refrigerant oil, a known refrigerant oil which has been used for a composition for a heat cycle system together with a working fluid comprising a halogenated hydrocarbon may be used without any particular restrictions. The refrigerant oil may, for example, be specifically an oxygen-containing synthetic oil (such as an ester refrigerant oil or an ether refrigerant oil), a fluorinated refrigerant oil, a mineral refrigerant oil or a hydrocarbon synthetic oil.

The ester refrigerant oil may, for example, be a dibasic acid ester oil, a polyol ester oil, a complex ester oil or a polyol carbonate oil.

The dibasic acid ester oil is preferably an ester of a $C_{5-10}$ dibasic acid (such as glutaric acid, adipic acid, pimelic acid, suberic acid, azelaic acid or sebacic acid) with a $C_{1-15}$ monohydric alcohol which is linear or has a branched alkyl group (such as methanol, ethanol, propanol, butanol, pentanol, hexanol, heptanol, octanol, nonanol, decanol, undecanol, dodecanol, tridecanol, tetradecanol or pentadecanol). Specifically, ditridecyl glutarate, di(2-ethylhexyl) adipate, diisodecyl adipate, ditridecyl adipate or di(3-ethylhexyl) sebacate may, for example, be mentioned.

The polyol ester oil is preferably an ester of a diol (such as ethylene glycol, 1,3-propanediol, propylene glycol, 1,4-butanediol, 1,2-butandiol, 1,5-pentadiol, neopentyl glycol, 1,7-heptanediol or 1,12-dodecanediol) or a polyol having from 3 to 20 hydroxy groups (such as trimethylolethane, trimethylolpropane, trimethylolbutane, pentaerythritol, glycerin, sorbitol, sorbitan or a sorbitol/glycerin condensate) with a $C_{6-20}$ fatty acid (such as a linear or branched fatty acid such as hexanoic acid, heptanoic acid, octanoic acid, nonanoic acid, decanoic acid, undecanoic acid, dodecanoic acid, eicosanoic acid or oleic acid, or a so-called neo acid having a quaternary α carbon atom).

The polyol ester oil may have a free hydroxy group.

The polyol ester oil is preferably an ester (such as trimethylolpropane tripelargonate, pentaerythritol 2-ethylhexanoate or pentaerythritol tetrapelargonate) of a hindered alcohol (such as neopentyl glycol, trimethylolethane, trimethylolpropane, trimethylolbutane or pentaerythritol).

The complex ester oil is an ester of a fatty acid and a dibasic acid, with a monohydric alcohol and a polyol. The fatty acid, the dibasic acid, the monohydric alcohol and the polyol may be as defined above.

The polyol carbonate oil is an ester of carbonic acid with a polyol.

The polyol may be the above-described diol or the above-described polyol. Further, the polyol carbonate oil may be a ring-opening polymer of a cyclic alkylene carbonate.

The ether refrigerant oil may be a polyvinyl ether oil or a polyoxyalkylene oil.

The polyvinyl ether oil may be one obtained by polymerizing a vinyl ether monomer such as an alkyl vinyl ether, or a copolymer obtained by copolymerizing a vinyl ether monomer and a hydrocarbon monomer having an olefinic double bond.

The vinyl ether monomer may be used alone or in combination of two or more.

The hydrocarbon monomer having an olefinic double bond may, for example, be ethylene, propylene, various forms of butene, various forms of pentene, various forms of hexene, various forms of heptene, various forms of octene, diisobutylene, triisobutylene, styrene, α-methylstyrene or alkyl-substituted styrene. The hydrocarbon monomer having an olefinic double bond may be used alone or in combination of two or more.

The polyvinyl ether copolymer may be either of a block copolymer and a random copolymer. The polyvinyl ether oil may be used alone or in combination of two or more.

The polyoxyalkylene oil may, for example, be a polyoxyalkylene monool, a polyoxyalkylene polyol, an alkyl ether of a polyoxyalkylene monool or a polyoxyalkylene polyol, or an ester of a polyoxyalkylene monool or a polyoxyalkylene polyol.

The polyoxyalkylene monool or the polyoxyalkylene polyol may be one obtained by e.g. a method of subjecting a $C_{2-4}$ alkylene oxide (such as ethylene oxide or propylene oxide) to ring-opening addition polymerization to an initiator such as water or a hydroxy group-containing compound in the presence of a catalyst such as an alkali hydroxide. Further, one molecule of the polyoxyalkylene chain may contain single oxyalkylene units or two or more types of oxyalkylene units. It is preferred that at least oxypropylene units are contained in one molecule.

The initiator to be used for the reaction may, for example, be water, a monohydric alcohol such as methanol or butanol, or a polyhydric alcohol such as ethylene glycol, propylene glycol, pentaerythritol or glycerol.

The polyoxyalkylene oil is preferably an alkyl ether or ester of a polyoxyalkylene monool or polyoxyalkylene polyol. Further, the polyoxyalkylene polyol is preferably a polyoxyalkylene glycol. Particularly preferred is an alkyl ether of a polyoxyalkylene glycol having the terminal hydroxy group of the polyoxyalkylene glycol capped with an alkyl group such as a methyl group, which is called a polyglycol oil.

The fluorinated refrigerant oil may, for example, be a compound having hydrogen atoms of a synthetic oil (such as the after-mentioned mineral oil, poly-α-olefin, alkylbenzene or alkylnaphthalene) substituted by fluorine atoms, a perfluoropolyether oil or a fluorinated silicone oil.

The mineral refrigerant oil may, for example, be a naphthene mineral oil or a paraffin mineral oil obtained by purifying a refrigerant oil fraction obtained by atmospheric distillation or vacuum distillation of crude oil by a purification treatment (such as solvent deasphalting, solvent extraction, hydrocracking, solvent dewaxing, catalytic dewaxing, hydrotreating or clay treatment) optionally in combination.

The hydrocarbon synthetic oil may, for example, be a poly-α-olefin, an alkylbenzene or an alkylnaphthalene.

The refrigerant oil may be used alone or in combination of two or more.

The refrigerant oil is preferably at least one member selected from a polyol ester oil, a polyvinyl ether oil and a polyglycol oil in view of compatibility with the working fluid.

The content of the refrigerant oil in the composition for a heat cycle system is not limited within a range not to remarkably decrease the effects of the present invention, and is preferably from 10 to 100 parts by mass, more preferably from 20 to 50 parts by mass, per 100 parts by mass of the working fluid.

<Other Optional Component>

The stabilizer optionally contained in the composition for a heat cycle system is a component which improves the stability of the working fluid against heat and oxidation. As the stabilizer, a known stabilizer which has been used for a heat cycle system together with a working fluid comprising a halogenated hydrocarbon, for example, an oxidation resistance-improving agent, a heat resistance-improving agent or a metal deactivator, may be used without any particular restrictions.

The oxidation resistance-improving agent and the heat resistance-improving agent may, for example, be N,N'-diphenylphenylenediamine, p-octyldiphenylamine, p,p'-dioctyldiphenylamine, N-phenyl-1-naphthylamine, N-phenyl-2-naphthylamine, N-(p-dodecyl)phenyl-2-naphthylamine, di-1-naphthylamine, di-2-naphthylamine, N-alkylphenothiazine, 6-(t-butyl)phenol, 2,6-di-(t-butyl)phenol, 4-methyl-2,6-di-(t-butyl)phenol or 4,4'-methylenebis(2,6-di-t-butylphenol). Each of the oxidation resistance-improving agent and the heat resistance-improving agent may be used alone or in combination of two or more.

The metal deactivator may, for example, be imidazole, benzimidazole, 2-mercaptobenzothiazole, 2,5-dimercaptothiadiazole, salicylidene-propylenediamine, pyrazole, benzotriazole, tritriazole, 2-methylbenzamidazole, 3,5-dimethylpyrazole, methylenebis-benzotriazole, an organic acid or an ester thereof, a primary, secondary or tertiary aliphatic amine, an amine salt of an organic acid or inorganic acid, a heterocyclic nitrogen-containing compound, an amine salt of an alkyl phosphate, or a derivative thereof.

The content of the stabilizer in the composition for a heat cycle system is not limited within a range not to remarkably decrease the effects of the present invention, and is preferably at most 5 parts by mass, more preferably at most 1 part by mass per 100 parts by mass of the working fluid.

The leak detecting substance optionally contained in the composition for a heat cycle system may, for example, be an ultraviolet fluorescent dye, an odor gas or an odor masking agent.

The ultraviolet fluorescent dye may be known ultraviolet fluorescent dyes which have been used for a heat cycle system together with a working fluid comprising a halogenated hydrocarbon, such as dyes as disclosed in e.g. U.S. Pat. No. 4,249,412, JP-A-10-502737, JP-A-2007-511645, JP-A-2008-500437 and JP-A-2008-531836.

The odor masking agent may be known perfumes which have been used for a heat cycle system together with a working fluid comprising a halogenated hydrocarbon, such as perfumes as disclosed in e.g. JP-A-2008-500437 and JP-A-2008-531836.

In a case where the leak detecting substance is used, a solubilizing agent which improves the solubility of the leak detecting substance in the working fluid may be used.

The solubilizing agent may be ones as disclosed in e.g. JP-A-2007-511645, JP-A-2008-500437 and JP-A-2008-531836.

The content of the leak detecting substance in the composition for a heat cycle system is not particularly limited within a range not to remarkably decrease the effects of the present invention, and is preferably at most 2 parts by mass, more preferably at most 0.5 part by mass per 100 parts by mass of the working fluid.

[Heat Cycle System]

The heat cycle system of the present invention is a system employing the composition for a heat cycle system of the present invention. The heat cycle system of the present invention may be a heat pump system utilizing heat obtained by a condenser or may be a refrigerating cycle system utilizing coldness obtained by an evaporator.

The heat cycle system of the present invention may, for example, be specifically a refrigerator, an air-conditioning apparatus, a power generation system, a heat transfer apparatus and a secondary cooling machine. Among them, the heat cycle system of the present invention, which stably and safely exhibits heat cycle performance in a working environment at higher temperature, is preferably employed as an air-conditioning apparatus to be disposed outdoors in many cases. Further, the heat cycle system of the present invention is preferably employed also for a refrigerating apparatus.

The air-conditioning apparatus may, for example, be specifically a room air-conditioner, a package air-conditioner (such as a store package air-conditioner, a building package air-conditioner or a plant package air-condition, a gas engine heat pump, a train air-conditioning system or an automobile air-conditioning system.

The refrigerator may, for example, be specifically a showcase (such as a built-in showcase or a separate showcase), an industrial fridge freezer, a vending machine or an ice making machine.

The power generation system is preferably a power generation system by Rankine cycle system.

The power generation system may, for example, be specifically a system wherein in an evaporator, a working fluid is heated by e.g. geothermal energy, solar heat or waste heat in a medium-to-high temperature range at a level of from 50 to 200° C., and the vaporized working fluid in a high temperature and high pressure state is adiabatically expanded by an expansion device, so that a power generator is driven by the work generated by the adiabatic expansion to carry out power generation.

Further, the heat cycle system of the present invention may be a heat transport apparatus. The heat transport apparatus is preferably a latent heat transport apparatus.

The latent heat transport apparatus may, for example, be a heat pipe conducting latent heat transport utilizing evaporation, boiling, condensation, etc. of a working fluid filled in an apparatus, and a two-phase closed thermosiphon. A heat pipe is applied to a relatively small-sized cooling apparatus such as a cooling apparatus of a heating portion of a semiconductor device and electronic equipment. A two-phase closed thermosiphon is widely used for a gas/gas heat exchanger, to accelerate snow melting and to prevent freezing of roads, since it does not require a wick and its structure is simple.

At the time of operation of the heat cycle system, in order to avoid drawbacks due to inclusion of moisture or inclusion of non-condensing gas such as oxygen, it is preferred to provide a means to suppress such inclusion.

If moisture is included in the heat cycle system, a problem may occur particularly when the heat cycle system is used at low temperature. For example, problems such as freezing in a capillary tube, hydrolysis of the working fluid or the refrigerant oil, deterioration of materials by an acid component formed in the cycle, formation of contaminants, etc. may arise. Particularly, if the refrigerant oil is a polyglycol oil or a polyol ester oil, it has extremely high moisture absorbing properties and is likely to undergo hydrolysis, and inclusion of moisture decreases properties of the refrigerant oil and may be a great cause to impair the long term reliability of a compressor. Accordingly, in order to suppress hydrolysis of the refrigerant oil, it is necessary to control the moisture concentration in the heat cycle system.

As a method of controlling the moisture concentration in the heat cycle system, a method of using a moisture-removing means such as a desiccating agent (such as silica gel, activated aluminum or zeolite) may be mentioned. The desiccating agent is preferably brought into contact with the composition for a heat cycle system in a liquid state, in view of the dehydration efficiency. For example, the desiccating agent is located at the outlet of the condenser 12 or at the inlet of the evaporator 14 to be brought into contact with the composition for a heat cycle system.

The desiccating agent is preferably a zeolite desiccating agent in view of chemical reactivity of the desiccating agent and the composition for a heat cycle system, and the moisture absorption capacity of the desiccating agent.

The zeolite desiccating agent is, in a case where a refrigerant oil having a large moisture absorption as compared with a conventional mineral refrigerant oil is used, preferably a zeolite desiccating agent containing a compound represented by the following formula (3) as the main component in view of excellent moisture absorption capacity.

$$M_{2/n}O \cdot Al_2O_3 \cdot xSiO_2 \cdot yH_2O \qquad (3)$$

wherein M is a group 1 element such as Na or K or a group 2 element such as Ca, n is the valence of M, and x and y are values determined by the crystal structure. The pore size can be adjusted by changing M.

To select the desiccating agent, the pore size and the fracture strength are important.

In a case where a desiccating agent having a pore size larger than the molecular size of the working fluid contained in the composition for a heat cycle system is used, the working fluid is adsorbed in the desiccating agent and as a result, chemical reaction between the working fluid and the desiccating agent will occur, thus leading to undesired phenomena such as formation of non-condensing gas, a decrease in the strength of the desiccating agent, and a decrease in the adsorption capacity.

Accordingly, it is preferred to use as the desiccating agent a zeolite desiccating agent having a small pore size. Particularly preferred is sodium/potassium type A synthetic zeolite having a pore size of at most 3.5 Å. By using a sodium/potassium type A synthetic zeolite having a pore size smaller than the molecular size of the working fluid, it is possible to selectively adsorb and remove only moisture in the heat cycle system without adsorbing the working fluid. In other words, the working fluid is less likely to be adsorbed in the desiccating agent, whereby heat decomposition is less likely to occur and as a result, deterioration of materials constituting the heat cycle system and formation of contaminants can be suppressed.

The size of the zeolite desiccating agent is preferably from about 0.5 to about 5 mm, since if it is too small, a valve or a thin portion in pipelines of the heat cycle system may be clogged, and if it is too large, the drying capacity will be decreased. Its shape is preferably granular or cylindrical.

The zeolite desiccating agent may be formed into an optional shape by solidifying powdery zeolite by a binding agent (such as bentonite). So long as the desiccating agent is composed mainly of the zeolite desiccating agent, other desiccating agent (such as silica gel or activated alumina) may be used in combination.

The proportion of the zeolite desiccating agent based on the composition for a heat cycle system is not particularly limited.

If non-condensing gas is included in the heat cycle system, it has adverse effects such as heat transfer failure in the condenser or the evaporator and an increase in the working pressure, and it is necessary to suppress its inclusion as far as possible. Particularly, oxygen which is one of non-condensing gases reacts with the working fluid or the refrigerant oil and promotes their decomposition.

The non-condensing gas concentration is preferably at most 1.5 vol %, particularly preferably at most 0.5 vol % by the volume ratio based on the working fluid, in a gaseous phase of the working fluid.

According to the above-described heat cycle system of the present invention, which employs the working fluid of the present invention having high safety, practically sufficient heat cycle performance can be obtained while suppressing influence over global warming, and there is substantially no problem with respect to the temperature glide.

EXAMPLES

Now, the present invention will be described in further detail with reference to Examples. However, it should be understood that the present invention is by no means restricted to specific Examples.

Ex. 1 to 58

In Ex. 1 to 58, a working fluid having HFO-1123 and at least one member of HFO-1234yf, HFC-32 and HFC-134a mixed in a proportion as identified in Tables 4 to 7 was prepared, and by the above methods, the temperature glide, the discharge temperature difference and the refrigerating cycle performance (relative refrigerating capacity and relative coefficient of performance) were measured and calculated. The results are shown in Tables 4 to 7.

TABLE 4

| | Working fluid composition [mass %] | | | | | Evaluation | | |
|---|---|---|---|---|---|---|---|---|
| | HFO-1123 | HFC-32 | GWP | $RCOP_{R410A}$ | $RQ_{R410A}$ | Temperature glide [° C.] | Discharge temperature difference TΔ [° C.] | Heat of combustion [MJ/kg] |
| Ex. 1 | 10 | 90 | 607.5 | 1.00 | 1.12 | 0.4 | 21.0 | 9.5 |
| Ex. 2 | 20 | 80 | 540.1 | 0.99 | 1.15 | 0.6 | 19.2 | 9.5 |
| Ex. 3 | 30 | 70 | 472.6 | 0.99 | 1.17 | 0.7 | 17.3 | 9.6 |
| Ex. 4 | 40 | 60 | 405.1 | 0.98 | 1.19 | 0.6 | 15.3 | 9.6 |
| Ex. 5 | 50 | 50 | 337.7 | 0.97 | 1.21 | 0.5 | 13.2 | 9.7 |
| Ex. 6 | 60 | 40 | 270.2 | 0.97 | 1.22 | 0.3 | 11.2 | 9.7 |
| Ex. 7 | 70 | 30 | 202.7 | 0.96 | 1.22 | 0.1 | 9.2 | 9.8 |
| Ex. 8 | 80 | 20 | 135.2 | 0.95 | 1.22 | 0.0 | 7.3 | 9.8 |
| Ex. 9 | 90 | 10 | 67.8 | 0.95 | 1.20 | 0.0 | 5.4 | 9.9 |

TABLE 5

| | Working fluid composition [mass %] | | | | | Evaluation | | |
|---|---|---|---|---|---|---|---|---|
| | HFO-1123 | HFO-1234yf | GWP | $RCOP_{R410A}$ | $RQ_{R410A}$ | Temperature glide [° C.] | Discharge temperature difference TΔ [° C.] | Heat of combustion [MJ/kg] |
| Ex. 10 | 10 | 90 | 3.6 | 1.04 | 0.47 | 3.2 | −19.5 | 10.6 |
| Ex. 11 | 20 | 80 | 3.3 | 1.01 | 0.55 | 5.8 | −16.0 | 10.5 |
| Ex. 12 | 30 | 70 | 2.9 | 1.00 | 0.63 | 7.3 | −12.6 | 10.5 |
| Ex. 13 | 40 | 60 | 2.5 | 0.99 | 0.71 | 7.7 | −9.8 | 10.4 |
| Ex. 14 | 50 | 50 | 2.2 | 0.98 | 0.79 | 7.2 | −7.3 | 10.3 |
| Ex. 15 | 60 | 40 | 1.8 | 0.97 | 0.86 | 6.0 | −5.2 | 10.2 |
| Ex. 16 | 70 | 30 | 1.4 | 0.96 | 0.94 | 4.3 | −3.2 | 10.1 |
| Ex. 17 | 80 | 20 | 1.0 | 0.95 | 1.02 | 2.4 | −1.4 | 10.1 |
| Ex. 18 | 90 | 10 | 0.7 | 0.95 | 1.10 | 0.9 | 0.8 | 10.0 |

TABLE 6

| | Working fluid composition [mass %] | | | | | Evaluation | | |
|---|---|---|---|---|---|---|---|---|
| | HFO-1123 | HFC-134a | GWP | $RCOP_{R410A}$ | $RQ_{R410A}$ | Temperature glide [° C.] | Discharge temperature difference TΔ [° C.] | Heat of combustion [MJ/kg] |
| Ex. 19 | 60 | 40 | 572.2 | 0.99 | 0.83 | 7.3 | 0.0 | 8.4 |
| Ex. 20 | 70 | 30 | 429.2 | 0.98 | 0.91 | 6.0 | 1.3 | 8.8 |
| Ex. 21 | 80 | 20 | 286.2 | 0.96 | 0.99 | 4.3 | 2.3 | 9.1 |
| Ex. 22 | 90 | 10 | 143.3 | 0.95 | 1.08 | 2.2 | 2.9 | 9.5 |

TABLE 7

| | Working fluid composition [mass %] | | | | | | Evaluation | | |
|---|---|---|---|---|---|---|---|---|---|
| | HFO-1123 | HFC-32 | HFO-1234yf | GWP | RCOP$_{R410A}$ | RQ$_{R410A}$ | Temperature glide [° C.] | Discharge temperature difference TΔ [° C.] | Heat of combustion [MJ/kg] |
| Ex. 23 | 10 | 10 | 80 | 70.7 | 1.02 | 0.56 | 5.0 | −14.4 | 10.5 |
| Ex. 24 | 20 | 10 | 70 | 70.4 | 1.01 | 0.64 | 6.7 | −10.8 | 10.4 |
| Ex. 25 | 30 | 10 | 60 | 70.0 | 1.00 | 0.72 | 7.4 | −7.8 | 10.3 |
| Ex. 26 | 40 | 10 | 50 | 69.6 | 0.99 | 0.80 | 7.2 | −5.2 | 10.3 |
| Ex. 27 | 50 | 10 | 40 | 69.3 | 0.98 | 0.88 | 6.2 | −2.9 | 10.2 |
| Ex. 28 | 60 | 10 | 30 | 68.9 | 0.97 | 0.96 | 4.4 | −0.9 | 10.1 |
| Ex. 29 | 70 | 10 | 20 | 68.5 | 0.96 | 1.04 | 2.9 | 0.9 | 10.0 |
| Ex. 30 | 80 | 10 | 10 | 68.1 | 0.95 | 1.12 | 1.2 | 2.9 | 9.9 |
| Ex. 31 | 10 | 20 | 70 | 137.8 | 1.02 | 0.65 | 5.8 | −9.3 | 10.4 |
| Ex. 32 | 20 | 20 | 60 | 137.5 | 1.01 | 0.73 | 6.7 | −6.1 | 10.3 |
| Ex. 33 | 30 | 20 | 50 | 137.1 | 1.00 | 0.81 | 6.8 | −3.3 | 10.2 |
| Ex. 34 | 40 | 20 | 40 | 136.7 | 0.99 | 0.89 | 6.1 | −0.9 | 10.1 |
| Ex. 35 | 50 | 20 | 30 | 136.4 | 0.98 | 0.97 | 4.9 | 1.2 | 10.0 |
| Ex. 36 | 60 | 20 | 20 | 136.0 | 0.97 | 1.05 | 3.2 | 3.1 | 10.0 |
| Ex. 37 | 70 | 20 | 10 | 135.6 | 0.96 | 1.13 | 1.4 | 5.0 | 9.9 |
| Ex. 38 | 10 | 30 | 60 | 204.9 | 1.02 | 0.72 | 5.7 | −4.6 | 10.2 |
| Ex. 39 | 20 | 30 | 50 | 204.6 | 1.01 | 0.81 | 6.1 | −1.7 | 10.2 |
| Ex. 40 | 30 | 30 | 40 | 204.2 | 1.00 | 0.89 | 5.8 | 0.9 | 10.1 |
| Ex. 41 | 40 | 30 | 30 | 203.8 | 0.99 | 0.97 | 4.8 | 3.2 | 10.0 |
| Ex. 42 | 50 | 30 | 20 | 203.5 | 0.98 | 1.05 | 3.3 | 5.2 | 9.9 |
| Ex. 43 | 60 | 30 | 10 | 203.1 | 0.97 | 1.14 | 1.7 | 7.1 | 9.8 |
| Ex. 44 | 10 | 40 | 50 | 272.0 | 1.02 | 0.80 | 5.2 | −0.2 | 10.1 |
| Ex. 45 | 20 | 40 | 40 | 271.7 | 1.01 | 0.88 | 5.2 | 2.6 | 10.0 |
| Ex. 46 | 30 | 40 | 30 | 271.3 | 0.99 | 0.96 | 4.5 | 1.4 | 9.9 |
| Ex. 47 | 40 | 40 | 20 | 270.9 | 0.98 | 1.04 | 3.3 | 7.1 | 9.9 |
| Ex. 48 | 50 | 40 | 10 | 270.6 | 0.97 | 1.13 | 1.8 | 10.1 | 9.8 |
| Ex. 49 | 10 | 50 | 40 | 339.1 | 1.01 | 0.87 | 4.4 | 4.1 | 10.0 |
| Ex. 50 | 20 | 50 | 30 | 338.8 | 1.00 | 0.95 | 4.0 | 6.7 | 9.9 |
| Ex. 51 | 30 | 50 | 20 | 338.4 | 0.99 | 1.03 | 3.2 | 9.0 | 9.8 |
| Ex. 52 | 40 | 50 | 10 | 338.0 | 0.98 | 1.12 | 1.9 | 11.2 | 9.7 |
| Ex. 53 | 10 | 60 | 30 | 406.2 | 1.01 | 0.94 | 3.4 | 8.2 | 9.8 |
| Ex. 54 | 20 | 60 | 20 | 405.9 | 1.00 | 1.02 | 2.8 | 10.8 | 9.8 |
| Ex. 55 | 30 | 60 | 10 | 405.5 | 0.99 | 1.10 | 1.9 | 13.1 | 9.7 |
| Ex. 56 | 10 | 70 | 20 | 473.3 | 1.01 | 1.00 | 2.3 | 12.4 | 9.7 |
| Ex. 57 | 20 | 70 | 10 | 473.0 | 1.00 | 1.09 | 1.7 | 14.9 | 9.6 |
| Ex. 58 | 10 | 80 | 10 | 540.4 | 1.00 | 1.06 | 1.3 | 16.6 | 9.6 |

Ex. 59 to 94

In Ex. 59 to 94, a working fluid having HFO-1123, HFO-1234ze(E) and HFC-32 mixed in a proportion as identified in Table 8 was prepared, and by the above methods, the temperature glide, the discharge temperature difference and the refrigerating cycle performance (relative refrigerating capacity and relative coefficient of performance) were measured and calculated. The results are shown in Table 8.

TABLE 8

| | Working fluid composition [mass %] | | | | | | Evaluation | | |
|---|---|---|---|---|---|---|---|---|---|
| | HFO-1123 | HFC-32 | HFO-1234ze(E) | GWP | RCOP$_{R410A}$ | RQ$_{R410A}$ | Temperature glide [° C.] | Discharge temperature difference TΔ [° C.] | Heat of combustion [MJ/kg] |
| Ex. 59 | 10 | 10 | 80 | 72.3 | 1.05 | 0.47 | 8.0 | −11.4 | 10.0 |
| Ex. 60 | 20 | 10 | 70 | 71.8 | 1.04 | 0.55 | 9.1 | −7.6 | 10.0 |
| Ex. 61 | 30 | 10 | 60 | 71.2 | 1.03 | 0.63 | 11.6 | −4.4 | 10.0 |
| Ex. 62 | 40 | 10 | 50 | 70.6 | 1.02 | 0.71 | 10.7 | −1.8 | 10.0 |
| Ex. 63 | 50 | 10 | 40 | 70.1 | 1.00 | 0.80 | 10.7 | 0.4 | 9.9 |
| Ex. 64 | 60 | 10 | 30 | 69.5 | 0.98 | 0.88 | 8.8 | 2.2 | 9.9 |
| Ex. 65 | 70 | 10 | 20 | 68.9 | 0.97 | 0.98 | 6.2 | 3.6 | 9.9 |
| Ex. 66 | 80 | 10 | 10 | 68.3 | 0.96 | 1.09 | 3.1 | 4.5 | 9.9 |
| Ex. 67 | 10 | 20 | 70 | 139.2 | 1.05 | 0.56 | 9.7 | −5.9 | 9.9 |
| Ex. 68 | 20 | 20 | 60 | 138.7 | 1.04 | 0.64 | 9.9 | −2.6 | 9.9 |
| Ex. 69 | 30 | 20 | 50 | 138.1 | 1.02 | 0.73 | 11.1 | 0.1 | 9.9 |
| Ex. 70 | 40 | 20 | 40 | 137.5 | 1.00 | 0.81 | 9.7 | 2.4 | 9.9 |
| Ex. 71 | 50 | 20 | 30 | 137.0 | 0.99 | 0.90 | 8.7 | 4.3 | 9.9 |
| Ex. 72 | 60 | 20 | 20 | 136.4 | 0.97 | 0.99 | 6.3 | 5.6 | 9.8 |
| Ex. 73 | 70 | 20 | 10 | 135.8 | 0.96 | 1.10 | 3.2 | 6.6 | 9.8 |
| Ex. 74 | 10 | 30 | 60 | 206.1 | 1.04 | 0.65 | 9.9 | −1.1 | 9.9 |
| Ex. 75 | 20 | 30 | 50 | 205.6 | 1.03 | 0.73 | 9.6 | 1.8 | 9.9 |

TABLE 8-continued

| | Working fluid composition [mass %] | | | Evaluation | | | | | |
|---|---|---|---|---|---|---|---|---|---|
| | HFO-1123 | HFC-32 | HFO-1234ze(E) | GWP | $RCOP_{R410A}$ | $RQ_{R410A}$ | Temperature glide [° C.] | Discharge temperature difference TΔ [° C.] | Heat of combustion [MJ/kg] |
| Ex. 76 | 30 | 30 | 40 | 205.0 | 1.01 | 0.81 | 9.7 | 4.2 | 9.8 |
| Ex. 77 | 40 | 30 | 30 | 204.4 | 0.99 | 0.90 | 8.3 | 6.1 | 9.8 |
| Ex. 78 | 50 | 30 | 20 | 203.9 | 0.98 | 1.00 | 6.1 | 7.6 | 9.8 |
| Ex. 79 | 60 | 30 | 10 | 203.3 | 0.97 | 1.10 | 3.3 | 8.6 | 9.8 |
| Ex. 80 | 10 | 40 | 50 | 273.0 | 1.03 | 0.73 | 9.2 | 3.2 | 9.8 |
| Ex. 81 | 20 | 40 | 40 | 272.5 | 1.01 | 0.81 | 8.9 | 5.7 | 9.8 |
| Ex. 82 | 30 | 40 | 30 | 271.9 | 1.00 | 0.90 | 7.8 | 7.8 | 9.8 |
| Ex. 83 | 40 | 40 | 20 | 271.3 | 0.99 | 1.00 | 5.9 | 9.4 | 9.7 |
| Ex. 84 | 50 | 40 | 10 | 270.8 | 0.97 | 1.10 | 3.1 | 10.5 | 9.7 |
| Ex. 85 | 10 | 50 | 40 | 339.9 | 1.02 | 0.81 | 7.8 | 7.1 | 9.7 |
| Ex. 86 | 20 | 50 | 30 | 339.4 | 1.01 | 0.90 | 7.0 | 9.4 | 9.7 |
| Ex. 87 | 30 | 50 | 20 | 338.8 | 0.99 | 0.99 | 5.2 | 11.1 | 9.7 |
| Ex. 88 | 40 | 50 | 10 | 338.2 | 0.98 | 1.09 | 3.2 | 12.4 | 9.7 |
| Ex. 89 | 10 | 60 | 30 | 406.8 | 1.01 | 0.89 | 6.1 | 10.8 | 9.7 |
| Ex. 90 | 20 | 60 | 20 | 406.3 | 1.00 | 0.98 | 4.9 | 12.7 | 9.6 |
| Ex. 91 | 30 | 60 | 10 | 405.7 | 0.99 | 1.08 | 3.0 | 14.2 | 9.6 |
| Ex. 92 | 10 | 70 | 20 | 473.7 | 1.01 | 0.97 | 4.1 | 14.2 | 9.6 |
| Ex. 93 | 20 | 70 | 10 | 473.2 | 1.00 | 1.06 | 2.7 | 15.9 | 9.6 |
| Ex. 94 | 10 | 80 | 10 | 540.6 | 1.00 | 1.05 | 2.1 | 17.5 | 9.5 |

INDUSTRIAL APPLICABILITY

The composition for a heat cycle system of the present invention and the heat cycle system employing the composition, are useful for a refrigerator (such as a built-in showcase, a separate showcase, an industrial fridge freezer, a vending machine or an ice making machine), an air-conditioning apparatus (such as a room air-conditioner, a store package air-conditioner, a building package air-conditioner, a plant package air-conditioner, a gas engine heat pump, a train air-conditioning system or an automobile air-conditioning system), power generation system (such as exhaust heat recovery power generation) or a heat transport apparatus (such as a heat pipe).

This application is a continuation of PCT Application No. PCT/JP2015/051410, filed on Jan. 20, 2015, which is based upon and claims the benefit of priority from Japanese Patent Application No. 2014-030856 filed on Feb. 20, 2014. The contents of those applications are incorporated herein by reference in their entireties.

REFERENCE SYMBOLS

10: Refrigerating cycle system, 11: compressor, 12: condenser, 13: expansion valve, 14: evaporator, 15, 16: pump.

What is claimed is:

1. A composition for a heat cycle system, comprising:
trifluoroethylene (HFO 1123);
difluoromethane; and
1,3,3,3-tetrafluoropropene (HFO 1234ze);
wherein a total amount of HFO-1123 and HFO 1234ze based on the entire amount of the composition is at least 70 mass %, and
wherein a global warming potential of the composition according to the (100 years) Intergovernmental Panel on Climate Change (IPCC), Fourth assessment report, is less than 675.

2. The composition for a heat cycle system according to claim 1, wherein of the working fluid for heat cycle, the relative coefficient of performance ($RCOP_{R410A}$) calculated in accordance with the following formula (1) is from 0.85 to 1.20:

$$\text{Relative performance of coefficient } (RCOP_{R410A}) = \frac{\text{Coefficient of performance of sample } (COP_{sample})}{\text{Coefficient of performance of } R410A \ (COP_{R410A})} \quad (1)$$

wherein R410A is a mixture of difluoromethane and pentafluoroethane in a mass ratio of 1:1, and the sample is the working fluid to be subjected to relative evaluation; and the coefficient of performance of each of the sample and R410A is a value obtained by dividing the obtained output (kW) by the required power consumption (kW) when each of the sample and R410A is applied to a standard refrigerating cycle under conditions such that the evaporation temperature is −15° C. (in the case of a non-azeotropic mixture, the average temperature of the evaporation initiation temperature and the evaporation completion temperature), the condensing temperature is 30° C. (in the case of a non-azeotropic mixture, the average temperature of the condensation initiation temperature and the condensation completion temperature), the supercooling degree (SC) is 5° C., and the degree of superheat (SH) is 0° C.

3. The composition for a heat cycle system according to claim 1, wherein of the working fluid for heat cycle, the relative refrigerating capacity ($RQ_{R410A}$) calculated in accordance with the following formula (2) is from 0.70 to 1.50:

$$\text{Relative refrigerating capacity } (RQ_{R410A}) = \frac{\text{Refrigerating capacity of sample } (Q_{sample})}{\text{Refrigerating capacity of } R410A \ (Q_{R410A})} \quad (2)$$

wherein R410A is a mixture of difluoromethane and pentafluoroethane in a mass ratio of 1:1, and the sample is the working fluid to be subjected to relative evaluation; and the refrigerating capacity of each of the sample and R410A is an output (kW) when each of the sample and R410A is applied to a standard refrigerating cycle under conditions such that the evaporation temperature is −15° C. (in the case of a non-azeotropic mixture, the average temperature of the evaporation initiation temperature and the evaporation completion temperature), the condensing temperature is 30° C. (in the case of a non-azeotropic mixture, the average temperature of the condensation initiation temperature and the condensation completion temperature), the supercooling degree (SC) is 5° C., and the degree of superheat (SH) is 0° C.

4. The composition for a heat cycle system according to claim 1, wherein of the working fluid for heat cycle, the temperature glide is at most 8° C., which is represented by a difference between the evaporation initiation temperature and the evaporation completion temperature in an evaporator when applied to a standard refrigerating cycle under conditions such that the evaporation temperature is −15° C. (in the case of a non-azeotropic mixture, the average temperature of the evaporation initiation temperature and the evaporation completion temperature), the condensing temperature is 30° C. (in the case of a non-azeotropic mixture, the average temperature of the condensation initiation temperature and the condensation completion temperature), the supercooling degree (SC) is 5° C., and the degree of superheat (SH) is 0° C.

5. The composition for a heat cycle system according to claim 1, wherein the value (TΔ) is at most 30° C., which is obtained by subtracting the compressor discharge gas temperature ($T_{R410A}$) when a mixture of difluoromethane and pentafluoroethane in a mass ratio of 1:1 is applied to the following standard refrigerating cycle, from the compressor discharge gas temperature (Tx) when the working fluid for heat cycle is applied to the following standard refrigerating cycle, the standard refrigerating cycle being conducted under conditions such that the evaporation temperature is −15° C. (in the case of a non-azeotropic mixture, the average temperature of the evaporation initiation temperature and the evaporation completion temperature), the condensing temperature is 30° C. (in the case of a non-azeotropic mixture, the average temperature of the condensation initiation temperature and the condensation completion temperature), the supercooling degree (SC) is 5° C., and the degree of superheat (SH) is 0° C.

6. The composition for a heat cycle system according to claim 1, wherein the working fluid for heat cycle has a heat of combustion of less than 19 MJ/kg.

7. The composition for a heat cycle system according to claim 1, wherein a content of the trifluoroethylene is from 10 to 80 mass %, a content of the difluoromethane is from 10 to 80 mass %, and a content of the 1,3,3,3-tetrafluoropropene is from 5 to 45 mass %, based on the working fluid for heat cycle.

8. The composition for a heat cycle system according to claim 1, wherein a content of the trifluoroethylene is at least 20 mass % based on the working fluid for heat cycle.

9. The composition for a heat cycle system according to claim 1, wherein a content of the trifluoroethylene is from 20 to 80 mass % based on the working fluid for heat cycle.

10. The composition for a heat cycle system according to claim 1, wherein a content of the trifluoroethylene is from 40 to 60 mass % based on the working fluid for heat cycle.

11. A heat cycle system, which employs the composition for a heat cycle system according to claim 1.

12. The heat cycle system according to claim 11, which is a refrigerating apparatus, an air-conditioning apparatus, a power generation system, a heat transport apparatus or a secondary cooling machine.

* * * * *